United States Patent [19]

Marei

[11] Patent Number: 4,617,318

[45] Date of Patent: Oct. 14, 1986

[54] NON-IRRITATING PYRETHROID FORMULATIONS IN VEGETABLE OILS AND TALL OILS

[75] Inventor: Abdel H. Marei, Mercerville, N.J.

[73] Assignee: American Cyanamid Company, Stamford, Conn.

[21] Appl. No.: 305,759

[22] Filed: Sep. 25, 1981

[51] Int. Cl.$^4$ .................... A01N 37/34; A01N 53/00; A01N 37/10

[52] U.S. Cl. .................................. 514/520; 514/531; 514/532; 514/784

[58] Field of Search ...................... 424/304, 365, 308; 260/97.5; 514/531

[56] References Cited

U.S. PATENT DOCUMENTS

| | | | |
|---|---|---|---|
| 3,961,043 | 6/1976 | Huvar | 424/365 |
| 3,966,959 | 6/1976 | Addor | 424/304 |
| 4,199,595 | 4/1980 | Berkelhammer et al. | 424/304 |
| 4,310,542 | 1/1982 | Mortel et al. | 424/304 |

OTHER PUBLICATIONS

Handbook of Non-Description Drugs, 6th ed., pp. 286–287, 1980.

*Primary Examiner*—Donald B. Moyer
*Assistant Examiner*—John W. Rollins
*Attorney, Agent, or Firm*—Estelle J. Tsevdos

[57] ABSTRACT

Liquid pesticidal compositions comprising pyrethroid solutions in vegetable oils, fatty acids, mixtures of fatty acids, tall oils, and mixtures of vegetable oils with fatty acids and tall oils. Pyrethroid pesticidal solutions may optionally contain anionic, non-ionic surfactants, and mixtures thereof. A method of application is also described. These compositions are less irritating to mammalian ocular tissues than are similar conventional formulations.

10 Claims, No Drawings

NON-IRRITATING PYRETHROID FORMULATIONS IN VEGETABLE OILS AND TALL OILS

The invention herein described relates to certain liquid compositions of pyrethroid pesticides which are characterized by being markedly less irritating and destructive to the ocular tissues of mammals than would be comparable conventionally-prepared pesticidal compositions. Compositions of the invention comprise various pyrethroid pesticides in vegetable oils, fatty acids, mixtures of fatty acids, tall oils, and mixtures of vegetable oils with fatty acids and tall oils. These pyrethroid compositions may optionally contain anionic, non-ionic surfactants and mixtures thereof.

Various pyrethroids are valuable agricultural pesticides which are particularly useful for the control of a variety of insects. Unfortunately conventional liquid formulations of pyrethroids are known to irritate or even irreversibly damage ocular tissues of mammals. Under field conditions the handling and/or use of conventional pyrethroid formulations may be hazardous to the applicators of these pesticides. Control of insects and other pests in the agricultural industry is desirable by means of pyrethroids, but the occupational hazard of potential eye damage to handlers and applicators of the chemicals represents a significant problem. An object of this invention is to provide new and useful chemical formulations of pyrethroids which are effective pesticides yet less harmful to mammalian ocular tissues than are conventional formulations. This object is manifest in the following description and particularly delineated in the appended claims.

It has been discovered that certain pyrethroids may be added to vegetable oils, fatty acids, tall oils, and mixtures of vegetable oils with fatty acids and tall oils, and that such compositions are notably less damaging to mammalian ocular tissues than are conventional formulations. Compositions of the invention comprise a solution of a pyrethroid represented by the following structural formula:

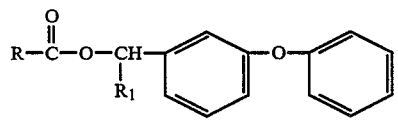

(I)

wherein $R_1$ is hydrogen or CN; R is

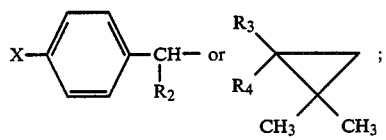

X is hydrogen, halogen, $C_1$-$C_3$ alkyl, $C_1$-$C_3$ alkoxy, $CF_3$, $CF_3O$— or $F_2CHO$—; $R_2$ is $C_1$-$C_4$ alkyl; $R_3$ is hydrogen, halogen or $C_1$-$C_2$ alkyl; $R_4$ is halogen, $C_1$-$C_2$ alkyl or $(Y)_2C$=CH— wherein Y is halogen, and when $R_3$ and $R_4$ are taken together with the carbon atom they are attached to they represent the moiety

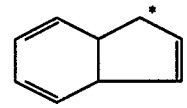

in which the carbon atom marked with an asterisk is shared both by said moiety and the cyclopropane ring it is attached to; and vegetable oils, liquid fatty acids or mixtures thereof. These solutions may optionally also contain surfactants and/or other agriculturally acceptable adjuvants.

Of special interest are the following compounds of formula (I):

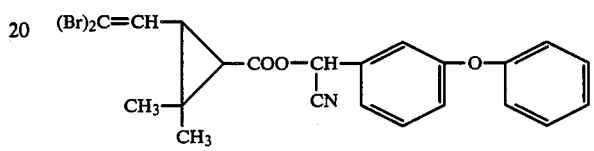

(−)-α-cyano-m-phenoxybenzyl cis-(+)-3-(2,2-dibromovinyl)-2,2-dimethylcyclopropane

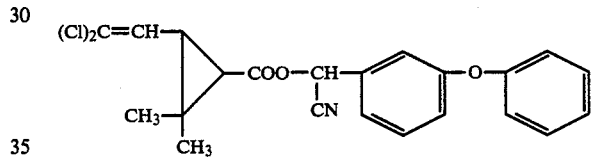

α-cyano-m-phenoxybenzyl 3-(2,2-dichlorovinyl)-2,2-dimethylcyclopropane carboxylate

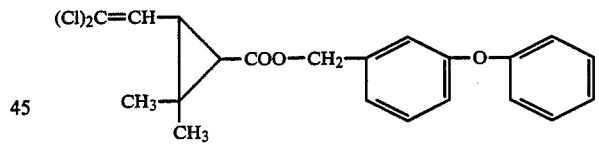

m-phenoxybenzyl 3-(2,2-dichlorovinyl)-2,2-dimethylcyclopropane carboxylate (generic name: permethrin)

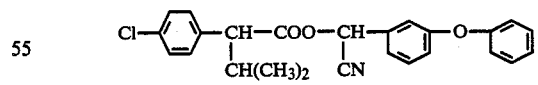

α-cyano-m-phenoxybenzyl 2-(p-chlorophenyl)-3-methylbutyrate (generic name: fenvalerate)

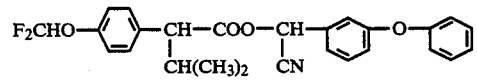

(±)-α-cyano-m-phenoxybenzyl (+)-2-[p-(difluoromethoxy)phenyl]-3-methylbutyrate

[Structure: α-cyano-m-phenoxybenzyl 3,3-dimethyl-spiro[cyclopropane-1,1'-indene]-2-carboxylate]

α-cyano-m-phenoxybenzyl 3,3-dimethyl-spiro[cyclopropane-1,1'-indene]-2-carboxylate (generic name: cypothrin)

By way of background, several of these chemicals are described in U.S. Pat. Nos. 4,062,968; 4,199,595; and 3,966,959 and United Kingdom Pat. No. 1,413,491.

Conventional formulations of some pyrethroids are known to irritate and otherwise damage mammalian eye tissues. For example, an emulsifiable concentrate comprising a blend of anionic/non-ionic surfactants and 300 g/l of the pyrethroid (±)-α-cyano-m-phenoxybenzyl (+)-2-(p-difluoro-methoxyphenyl)-3-methylbutyrate having the following structural formula:

[Structure: $F_2CHO$—phenyl—CH(CH(CH$_3$)$_2$)—COO—CH(CN)—phenyl—O—phenyl]

in an aromatic hydrocarbon solvent (95% aromatics; flash point TCC-min 100° F.; distillation range from about 290° F. to 340° F.; specific gravity of 0.853–0.875 at 15.56° C.) is an eye irritant and under certain conditions may cause irreversible ocular tissue damage. Formations similar to the above but containing the pyrethroid α-cyano-m-phenoxybenzyl 2-(p-chlorophenyl)-3-methylbutyrate also cause irreversible damage when brought in contact with mammalian ocular tissues.

The pyrethroids of formula I, and especially those of interest as indicated above, when dissolved in vegetable oils (i.e., soybean oil, corn oil, etc.), or in long chain liquid fatty acids and mixtures thereof, especially tall oils, or mixtures of vegetable oils and fatty acids, where such solutions may also contain anionic, non-ionic surfactants and mixtures thereof, cause only transient eye irritation when vegetable oils are used as solvents, and no eye irritation at all when the solvents are tall oils. Furthermore, such compositions tend to favorably alter the efficacy of formula-I compounds.

A representative composition of the invention is prepared by admixing the following on a weight basis: (1) about 5 to 45% of a compound of formula-I, such as (±)-α-cyano-m-phenoxybenzyl (+)-2-[p-difluoromethoxy)phenyl]-3-methylbutyrate; and (2) about 2 to 10% of a surfactant of sorbitan monolaurate, sorbitan monooleate, various anionic (sulfonate)/non-ionic blends and mixtures thereof; and (3) mixtures of vegetable oils and fatty acids in amounts sufficient to adjust the total composition to 100%; or similar amounts of a vegetable oil such as soybean oil, corn oil, or mixtures of fatty acids such as tall oils having the following ingredients and characteristics:

Moisture; %: <0.1
Ash; %: <0.001
Rosin Acids; %: 0.5–5.0
Unsaponifiables; %: 0.5–3.0
Fatty acids, total; %: 92.8–99.0
Linoleic acid, non-conjugated; %: 34–38
Linoleic acid, conjugated; %: 7–9
Oleic acid; %: 44–51
Saturated acids; %: 3–5
Stearic acid; %: 0–2
Other fatty acids; %: 2–8
Acid value: 190–198
Iodine value (Wijs): 130–131
Specific gravity, 25° C.: 0.897–0.906
Viscosity, SUS, 100° F.: 93–100

The resulting mixture is then stirred and heated, if necessary, until a clear homogeneous solution is obtained.

For ultra-low-volume aerial application (ULV) compositions are preferred which comprises on a weight basis about 20% to 40% and preferably 28% to 32% of a compound of formula-I and a vegetable oil or a tall oil of the above definition, or mixtures thereof, in amounts sufficient to adjust compositions to 100%. These undiluted liquid compositions are applied in situ at the rate of about 0.16 to 28 l/ha or from about 2 fluid ounces per acre to 3 gallons per acre. When such liquid compositions are applied at the rate of from about 28 to 37 l/ha or about 3 to 5 gallons per acre, such application is referred to as low-volume (LV) application.

A preferred formulation for either low-volume application or ultra-low-volume application comprises about 37% by weight of (±)-α-cyano-m-phenoxybenzyl (+)-2-[p-(difluoromethoxy)phenyl]-3-methylbutyrate and about 63% by weight of a vegetable oil of corn oil, soybean oil and cottonseed oil.

In practice, it is found that low-volume and ultra low volume applications of the undiluted compositions of the invention, applied as finely divided droplets having a mass median diameter between about 15 microns and 150 microns, generally provide more effective insect control for a longer period of time than can be achieved with an equivalent amount of the same insecticidal agent prepared as a conventional emulsifiable concentrate, wettable powder or flowable formulation, which is dispersed in water and applied at the rate of about 20 to 120 gallons per acre or about 187 to 1122 l/ha.

For use in the above formulations, the following formula-I compounds are preferred:

[Structure: $(Br)_2C=CH$—cyclopropane(CH$_3$,CH$_3$)—COO—CH(CN)—phenyl—O—phenyl]

(−)-α-cyano-m-phenoxybenzyl cis-(+)-3-(2,2-dibromovinyl)-2,2-dimethylcyclopropane

[Structure: $(Cl)_2C=CH$—cyclopropane(CH$_3$,CH$_3$)—COO—CH(CN)—phenyl—O—phenyl]

α-cyano-m-phenoxybenzyl 3-(2,2-dichlorovinyl)-2,2-dimethylcyclopropane carboxylate

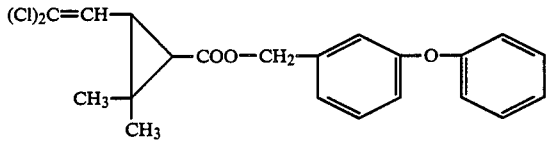

m-phenoxybenzyl 3-(2,2-dichlorovinyl)-2,2-dimethyl-cyclopropane carboxylate

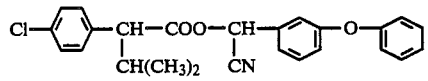

α-cyano-m-phenoxybenzyl 2-(p-chlorophenyl)-3-methylbutyrate

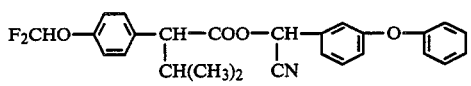

(±)-α-cyano-m-phenoxybenzyl (+)-2-[p-(difluoromethoxy)phenyl]-3-methylbutyrate

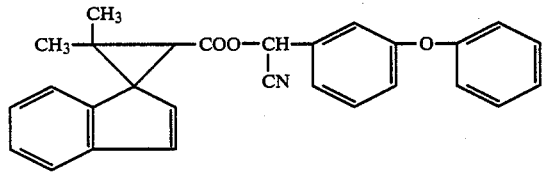

α-cyano-m-phenoxybenzyl 3,3-dimethyl-spiro[cyclopropane-1,1'-indene]-2-carboxylate For the control of insects, the compositions of the invention containing compounds of formula-I are applied at a rate of from about 50 to 150 g of active ingredient per hectare as dilute aqueous emulsions or as ultra-low-volume sprays.

Emulsifiable concentrates may be diluted with water at a rate of about 20 liters per hectare for aerial applications and up to 1,000 liters per hectare for ground applications. Alternatively, ultra-low-volume compositions may be used preferably for rapid and efficient distribution of formula-I compounds by aerial application. In general, emulsifiable concentrates in the form of dilute aqueous sprays are preferred for use on crops such as vegetables and fruit. Field crops (i.e., cotton) are best treated by aerial application of ULV formulations.

The following non-limiting examples further serve to illustrate the invention.

EXAMPLE 1

Evaluation of Mammalian Eye Irritation Caused by Pyrethroid Pesticides Solutions Pyrethroid test solutions are prepared by dissolving approximately 37 g aliquots of an 80.5% pure sample of (±)-α-cyano-m-phenoxybenzyl (+)-2[p-(difluoromethoxy)phenyl]-3-methylbutyrate in various solvents to yield approximately 30% test formulations of active compound on a weight basis. The percent weight ratios of pyrethroid and various solvents are given in Table I.

Pyrethroid test solutions are introduced into the conjunctival sac of male albino rabbits (New Zealand white) at a rate of 0.1 ml per test. Each test is replicated six times. The cornea, iris, and conjunctivae are observed for irritation reactions at one, two, three, and seven day intervals. Individual observations are averaged. The results of various experiments are presented in Table I. These data show that various pyrethroid formulations of the invention are either non-irritating or cause only reversible irritation of rabbit eye tissues.

TABLE I

Rabbit Eye Irritation Caused by Various Formulations of the Pyrethroid (±)α-cyano-m-phenoxybenzyl (+)-2[p-(difluoromethoxy)phenyl]-3-methylbutyrate

| Formulation No. | Pyrethroid % w/w | Solvent; % w/w | Rabbit Eye Irritation, Observation Based On Data Averaged Over 7 Days |
|---|---|---|---|
| 1 | 37.2 | Corn Oil; 62.8 | Reversible Irritation; Clear in 7 Days |
| 2 | 37.3 | Soybean Oil; 62.7 | Reversible Irritation; Clear in 7 Days |
| 3 | 37.86 | Tall Oil - Pure; 62.14 | Reversible Irritation; Clear in 72 Hours |
| 4 | 36.7 | Tall Oil - Crude; 63.3 | No Irritation |
| 5 | 37.75 | Tall Oil - Ave. Purity; 62.25 | No Irritation |

EXAMPLE 2

Evaluation of Eye Irritation Caused by Pyrethroid Solutions Using Male Albino Rabbits as Test Animals Using the method of Example 1, various pyrethroid solutions were prepared and evaluated. The results of this experiment are presented in Table II. These data show that a conventional pyrethroid formulation using an aromatic hydrocarbon solvent blend causes irreversible damage to eye tissues whereas formulations of the invention cause no eye irritation over a seven-day test period.

TABLE II

Rabbit Eye Irritation Caused by Various Formulations Containing the Pyrethroid (±)α-cyano-m-phenoxybenzyl (+)-2[p-(difluoromethoxy)phenyl]-3-methylbutyrate

| Formulation No. | Pyrethroid % w/w | Solvent % w/w | Rabbit Eye Irritation, Observation Based On Data Averaged Over 7 Days |
|---|---|---|---|
| 1 | 80.5 | 19.5[a] | No Irritation |
| 2 | 38.05 | 61.96[b] | Irreversible Irritation |
| 3 | 37.05 | 62.95[c] | No Irritation |
| 4 | 37.40 | 62.60[d] | No Irritation |

[a] = technical material, contains 19.5% inert impurities.
[b] = surfactant - solvent mixture of 10.21% w/w of sulfonate/non-ionic surfactant blends and 51.75% w/w of an aromatic hydrocarbon solvent blend (aromatics 95% flash point TCC - min 100° F.; distillation range: 290° F. to 340° F.; specific gravity at 15.56° C., 0.853–0.875).
[c] = surfactant - solvent mixture of 0.99% w/w of sorbitan monolaurate, 8.95% w/w of sorbitan monooleate and 53.01% w/w of tall oil.
[d] = as under [c], except that the components are used in 0.5% w/w, 4.82% w/w and 57.58% w/w quantities, respectively.

EXAMPLE 3

Evaluation of Insecticidal Activity of Pyrethroid Formulations

Various formulation of the pyrethroid (±)α-cyano-m-phenoxybenzyl (+)-2[p-(difluoromethoxy)phenyl]-3-methylbutyrate were prepared as previously described in Example 2. Young cotton plants (*Gossypium hirsutum*, L.) in the two-leaf stage are dipped in various concentrations of pyrethroid formulations diluted with deionized water. After drying the plants are maintained in the greenhouse under high-intensity daylight lamps. Care is taken to avoid wetting the foliage of treated plants when plants are watered during this exposure period. Leafs are removed after 3, 10 and 21 days exposure. Each treated leaf is fed to ten southern armyworms (*Spodoptera eridania*) in a petri dish using four replicates per treatment. The results of this experiment are presented in Table III. These data show that pyrethroid formulations of the invention have insecticidal activity at least as effective and generally more effective than the conventional pyrethroid formulation.

TABLE III

Southern Armyworm LC$_{50}$ Assay (Averaged)

| Formula No.* | LC$_{50}$ (PPM) Days Post-Treatment | | |
|---|---|---|---|
| | 3 | 10 | 21 |
| 2 | 6.4 | 10.6 | 11.4 |
| 3 | 3.3 | 4.3 | 8.7 |
| 4 | 4.6 | 6.1 | 11.0 |

*Formula numbers and compositions correspond to those described and tested in Example 2.

EXAMPLE 4

Evaluation of α-cyano-m-phenoxybenzyl 2-(p-chlorophenyl)-3-methylbutyrate in a Formulation of the Present Invention The pyrethroid α-cyano-m-phenoxybenzyl 2-(p-chlorophenyl)-3-methylbutyrate is evaluated by the procedure described in Example 1. Results of this experiment are presented in Table IV. These data indicate that the pyrethroid formulation of the invention using tall oils is not irritating to rabbit eye tissues, whereas the conventional pyrethroid formulation using an aromatic hydrocarbon solvent blend causes irreversible damage to ocular tissues.

TABLE IV

Rabbit Eye Irritation Caused by Various Formulation Containing the Pyrethroid α-cyano-m-phenoxybenzyl 2-(p-chlorophenyl)-3-methylbutyrate

| Formulation No. | Pyrethroid % w/w | Solvent % w/w | Rabbit Eye Irritation, Observation Based On Data Averaged Over 7 Days |
|---|---|---|---|
| 1 | 90 | 10$^a$ | Reversible Irritation; Clear in 7 Days |
| 2 | 33 | 67$^b$ | Irreversible Irritation |
| 3 | 33 | 67$^c$ | No Irritation |

$^a$ = technical material, contains 10% w/w inert impurities
$^b$ = surfactant - solvent mixture of 1% w/w of sorbitan monolaurate, 9% w/w of sorbitan monooleate and 57% w/w of an aromatic hydrocarbon solvent blend (aromatics 95%; flash point TCC min 100° F.; distillation range: 290° F. to 340° F.; specific gravity at 15.56° C.: 0.853–0.875).
$^c$ = as under $^b$, except that the aromatic hydrocarbon is replaced with tall oil.

What is claimed is:

1. A low eye-irritating composition comprising about 5% to 45% by weight of a pesticidal compound of the following structural formula:

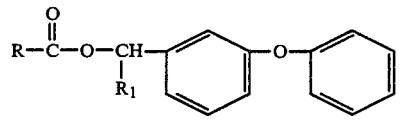

wherein R$_1$ is hydrogen or CN: R is

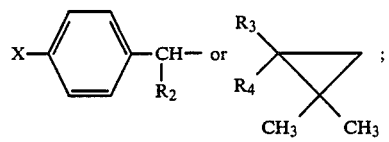

X is Cl, Br, CH$_3$—, CH$_3$O—, CF$_3$—, CF$_3$O— or F$_2$CHO; R$_2$ is C$_1$–C$_4$ alkyl; R$_3$ is H, Cl, Br or CH$_3$—; R$_4$ is Cl, Br, CH$_3$, (Cl)$_2$—C=CH— or (Br)$_2$C=CH—; and when R$_3$ and R$_4$ are taken together with the carbon atoms they are attached to, they represent the moiety

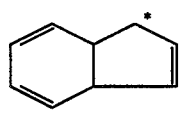

in which the carbon atom marked by an asterick is shared both by the moiety and the cyclopropane ring to which it is attached; and 2% to 10% by weight of the surfactant sorbitan monolaurate, sorbitan monooleate, or mixtures thereof, and a tall oil, in amounts sufficient to total the composition to 100%.

2. A composition according to claim 1, wherein the compound is (±)-α-cyano-m-phenoxybenzyl (+)-2-[p-(difluoromethoxy)phenyl]-3-methylbutyrate; and tall oil.

3. A composition according to claim 2 wherein the surfactant is a mixture of 1% sorbitan monolaurate and 9% sorbitan monooleate.

4. A composition according to claim 2, wherein the surfactant is a mixture of 0.5% sorbitan monolaurate and 4.5% sorbitan monooleate.

5. A composition according to claim 1, wherein the compound is α-cyano-m-phenoxybenzyl 2-(p-chlorophenyl)-3-methylbutyrate and tall oil.

6. A composition according to claim 5, wherein the surfactant is a mixture of 0.5% sorbitant monolaurate and 4.5% sorbitan monooleate.

7. A composition according to claim 1, wherein the compound is α-cyano-m-phenoxybenzyl-2-(p-chlorophenyl)-3-methylbutyrate; the surfactant is a mixture of 1% sorbitan monolaurate and 9% sorbitan monooleate and tall oil.

8. A method for the control of insects comprising applying to a locus in which insect control is desired about 0.15 to 37 l/ha, in the form of finely divided microns, of a low eye-irritating composition of about 5% to 45% by weight of a compound having the formula:

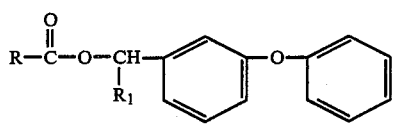

wherein R₁ is hydrogen or CN; R is

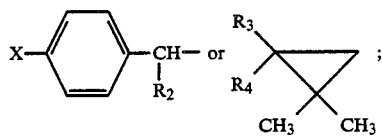

X is hydrogen, halogen, $C_1$-$C_3$ alkyl, $C_1$-$C_3$ alkoxy, $CF_3$, $CF_3O-$ or $F_2CHO$; $R_2$ is $C_1$-$C_4$ alkyl; $R_3$ is hydrogen, halogen or $C_1$-$C_2$ alkyl; $R_4$ is halogen, $C_1$-$C_2$ alkyl or $(y)_2=CH-$ and y is halogen, and when $R_3$ and $R_4$ are taken together with the carbon atoms they are attached to, they represent the moiety

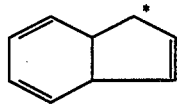

in which the carbon atom marked with an asterisk is shared both by said moiety and the cyclopropane ring to which it is attached; 2% to 10% by weight of sorbitan monolaurate, sorbitan monooleate, or mixtures thereof, and 45% to 90% by weight of a tall oil.

9. A method according to claim 8, wherein the compound is (±)-α-cyano-m-phenoxybenzyl (+)-2-[p-(difluoromethoxy)-phenyl]-3-methylbutyrate, and the composition is applied at a rate of from 0.16 to 28 l/ha.

10. A method according to claim 8, wherein the compound is α-cyano-m-phenoxy-benzyl-2-(p-chlorophenyl)-3-methylbutyrate, and the composition is applied at the rate of from 0.16 to 28 l/ha.

* * * * *